(12) United States Patent
Tanase et al.

(10) Patent No.: US 7,871,951 B2
(45) Date of Patent: Jan. 18, 2011

(54) MAGNESIUM COMPOUND, SOLID CATALYST COMPONENT, CATALYST FOR OLEFIN POLYMERIZATION AND METHOD OF PRODUCING POLYOLEFIN

(75) Inventors: Shojiro Tanase, Ichihara (JP); Nobuhiro Yabunouchi, Sodegaura (JP); Takanori Sadashima, Sumida-ku (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 0 days.

(21) Appl. No.: 12/408,926

(22) Filed: Mar. 23, 2009

(65) Prior Publication Data

US 2009/0186755 A1 Jul. 23, 2009

Related U.S. Application Data

(63) Continuation of application No. 11/573,047, filed as application No. PCT/JP05/15247 on Aug. 23, 2005, now abandoned.

(30) Foreign Application Priority Data

Aug. 24, 2004 (JP) .............................. 2004-243565

(51) Int. Cl.
*B01J 37/00* (2006.01)
*C08F 4/60* (2006.01)
(52) U.S. Cl. ...................... 502/111; 502/103; 502/117
(58) Field of Classification Search ................ 502/103
See application file for complete search history.

(56) References Cited

U.S. PATENT DOCUMENTS 4,663,299 A * 5/1987 Chadwick et al. ............. 502/9

| | 2008/0281059 A1 | 11/2008 | Tanase et al. |

FOREIGN PATENT DOCUMENTS

| EP | 0 184 347 | | 6/1986 |
| EP | 1108730 | * | 6/2001 |
| JP | 56-000811 | | 1/1981 |
| JP | 62-51633 | | 3/1987 |
| JP | 63-280707 | | 11/1988 |
| JP | 04-130107 | | 5/1992 |
| JP | 09-194522 | | 7/1997 |
| JP | 2001-233879 | | 8/2001 |
| JP | 2003-342217 | | 12/2003 |
| JP | 2004-210683 | | 7/2004 |
| WO | WO 2004/018529 | | 3/2004 |

OTHER PUBLICATIONS

U.S. Appl. No. 11/816,587, filed Aug. 17, 2007, Tanase, et al.

* cited by examiner

*Primary Examiner*—Melvin C Mayes
*Assistant Examiner*—Yun Qian
(74) *Attorney, Agent, or Firm*—Oblon, Spivak, McClelland, Maier & Neustadt, L.L.P.

(57) ABSTRACT

A method for producing magnesium compound represented by formula (I):

$$Mg(OEt)_{2-n}(OMe)_n \qquad (I)$$

where Et is an ethyl group, Me is a methyl group and n is a numerical value of from 0.001 to 1, by reacting metal magnesium, ethanol, methanol and a halogen and/or a halogen-containing compound containing at least 0.0001 gram atom of a halogen atom relative to one gram atom of the metal magnesium. A method of producing a solid catalyst component.

13 Claims, 1 Drawing Sheet

MAGNESIUM COMPOUND, SOLID CATALYST COMPONENT, CATALYST FOR OLEFIN POLYMERIZATION AND METHOD OF PRODUCING POLYOLEFIN

CROSS-REFERENCE TO RELATED APPLICATIONS

The present application is a Continuation application of U.S. application Ser. No. 11/573,047, filed Feb. 1, 2007, now abandoned; which is a 371 application of PCT/JP05/15247 filed Aug. 23, 2005, and claims foreign priority to Japan application 2004-243565, filed Aug. 24, 2004.

TECHNICAL FIELD

The invention relates to a magnesium compound which is useful for homopolymerization or copolymerization of an α-olefin such as ethylene and propylene, a solid catalyst component using the magnesium compound, a catalyst for olefin polymerization and a method of producing an olefin polymer.

TECHNICAL BACKGROUND

Hitherto, magnesium chloride and magnesium alkoxides have been widely used as a support material without being milled in the field of catalysts for olefin polymerization, specifically the homopolymerization or copolymerization of α-olefin such as ethylene and propylen. This may improve the catalyst activity and the morphology of polymer powder.

For example, for improving an obtained polymer in morphology including particle size, form, etc., there are known a method in which a magnesium compound is supported on an inorganic oxide such as silica (JP-A-S63-280707) and a method in which a magnesium compound once dissolved in a solvent such as an alcohol is precipitated again and the precipitate is used (JP-A-S58-000811). However, these methods include very complicated steps, since they require the procedures of supporting, dissolving and precipitating a magnesium compound. Further, these methods have a defect in that the catalyst is poor in performance stability.

The method of using as a support of catalysts a magnesium compound obtained by reacting metal magnesium, an alcohol such as ethanol and a certain amount of halogen (JP-A-H4-130107) has been developed. However, it has a problem in the point that the catalyst activity and the apparent density of the polymer powder obtained depends on the conditions.

In order to improve a polymerization activity and an appearance of film in ethylene polymerization, the method of using a support such as magnesium alkoxide pulverized mechanically (JP-A-H9-194522) has been disclosed.

However, the pulverization of a support causes increase in amount of fine powder contained in polymer powder, which reflects the properties of support particles, and bad powder form. A converting line may be blocked due to the increase in amount of fine powder. The flowability of powder may be lowered due to the bad powder form, thereby letting reactor operation unstable. Further the polymerization activity and controllability of molecular weight may be unsatisfactory.

In view of the above-mentioned problems, a purpose of the invention is to provide a magnesium compound which exhibits high activity without decrease of performances such as stereoregularity and appearance of film (fish-eye), are excellent in control of molecular weight and can give an olefin polymer excellent in apparent density; a solid catalyst component; a catalyst for olefin polymerization; and a method of producing an olefin polymer.

DISCLOSURE OF THE INVENTION

The inventors made efforts to attain the above-mentioned purposes, as the result, they found that the specific magnesium compound obtained by reacting a metal magnesium, ethanol, methanol and a halogen and/or a halogen-containing compound containing a predetermined amount of halogen atom as essential components is useful as a catalyst component. They also found that a catalyst for olefin polymerization comprising a solid catalyst component obtained by contacting the magnesium compound, a titanium compound, and, if necessary, a halide, an electron donating compound and an alcohol, an organometallic compound and an optional electron donating compound exhibits high activity, is excellent in control of molecular weight and can give an olefin polymer excellent in apparent density. The invention has been made based on the above findings.

The invention provides the following magnesium compound, solid catalyst component, catalyst for olefin polymerization and method of producing olefin polymer.

1. A magnesium compound represented by the formula (I) which is obtained by reacting metal magnesium, ethanol, methanol and a halogen and/or a halogen-containing compound containing at least 0.0001 gram atom of a halogen atom relative to one gram atom of the metal magnesium $$Mg(OEt)_{2-n}(OMe)_n \qquad (I)$$

where Et is an ethyl group, Me is a methyl group and n is a numerical value of from 0.001 to 1.

2. The magnesium compound according to 1, which has an average particle diameter $D_{50}$ of from 4 to 20 μm and a particle size distribution index (P) represented by the general formula (1) of P<4.0

$$P=(D_{90}/D_{10}) \qquad (1)$$

where $D_{90}$ is a particle diameter corresponding to 90% of cumulative weight fraction, and $D_{10}$ is a particle diameter corresponding to 10% of cumulative weight fraction.

3. The magnesium compound according to 1 or 2, wherein the halogen is iodine.
4. The magnesium compound according to 1 or 2, wherein the halogen-containing compound is magnesium dichloride.
5. The magnesium compound according to any one of 1 to 4, wherein n of the formula (I) is a numerical value of from 0.01 to 0.2.
6. A solid catalyst component obtained by reacting the following components (a) and (b):
(a) the magnesium compound according to any one of 1 to 5
(b) a titanium compound represented by the formula (II)

$$Ti(OR)_qX_{4-q} \qquad (II)$$

where X is a halogen atom, R is a hydrocarbon group having from 1 to 10 carbon atoms, q is an integer of from 0 to 4, and a plurality of R's are the same as or different from each other when q is 2 or more.

7. The solid catalyst component according to claim 6 obtained by reacting a halogen compound (c) and/or an electron donating compound (d) in addition to the components (a) and (b).
8. The solid catalyst component according to 6 obtained by reacting a halogen compound (c) and/or an alcohol (e) in addition to the components (a) and (b).
9. The solid catalyst component according to 7 or 8, wherein the halogen compound (c) is silicon tetrachloride.
10. The solid catalyst component for ethylene polymerization according to 8, wherein the alcohol (e) is isopropanol.

11. A catalyst for olefin polymerization comprising the following components (A) and (B):
(A) the solid catalyst component according to any one of 6 to 10
(B) an organometallic compound.
12. The catalyst for olefin polymerization according to 11 further comprising an electron donating compound (C).
13. A method of producing a polyolefin using the catalyst for olefin polymerization according to 11 or 12.

There can be produced an ethylene-based polymer that exhibits high polymerization activity, excellent controllability of molecular weight and high stereoregularity by using a catalyst for olefin polymerization using the magnesium compound of the invention. There can also be produced a polymer excellent in apparent density and morphology.

BEST MODE FOR CARRYING OUT THE INVENTION

Figure 1:
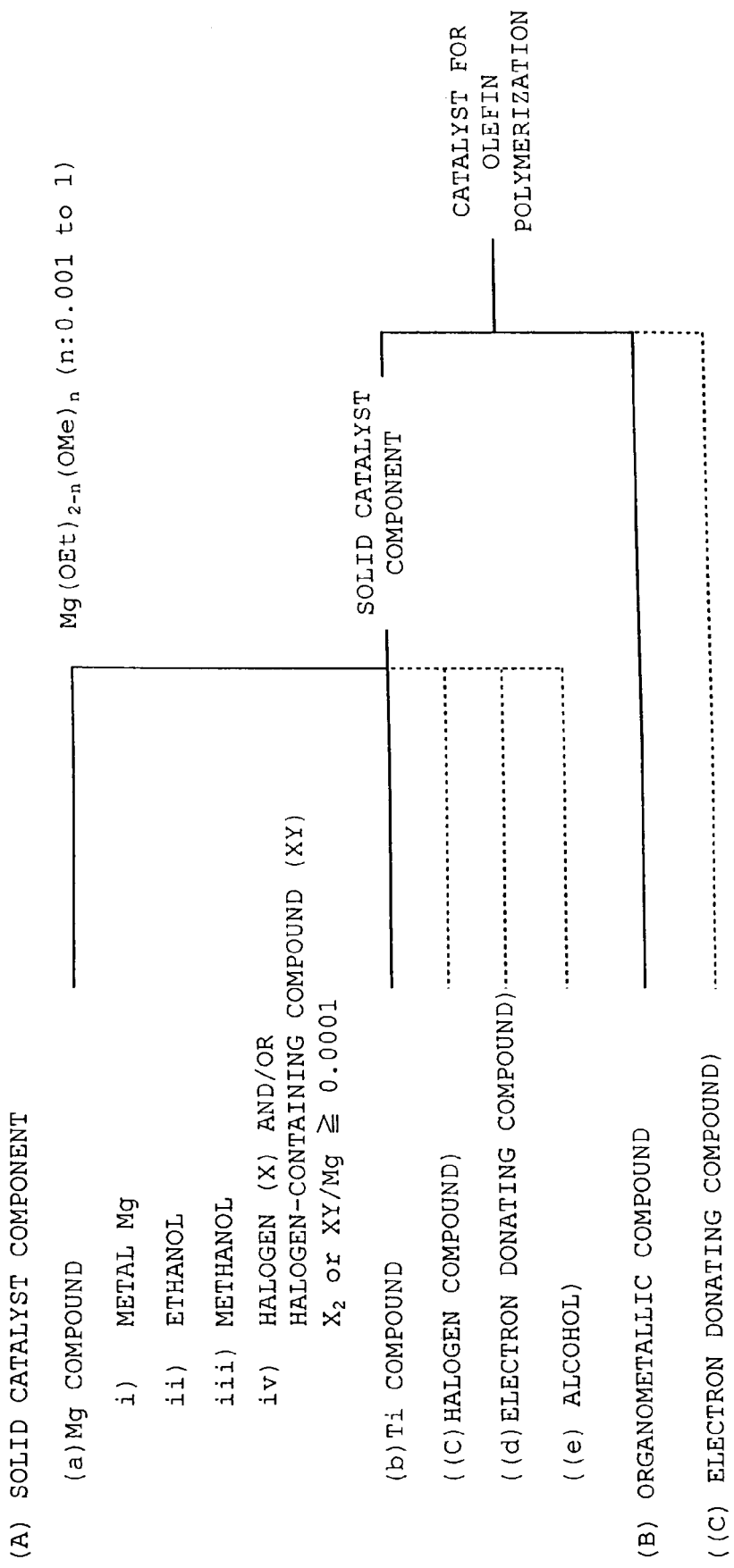
FIG. 1 is a drawing which shows the olefin-polymerization catalyst system of the invention.

FIG. 1 is a drawing which shows the olefin polymerization catalyst system including the magnesium compound of the invention. Now, the magnesium compound, the solid catalyst component and the catalyst for olefin polymerization will be explained.

[Magnesium Compound]

Firstly, the magnesium compound of the invention will be specifically explained.

The magnesium compound of the invention represented by the formula (I) which is obtained by reacting metal magnesium, ethanol, methanol and a halogen and/or a halogen-containing compound containing at least 0.0001 gram atom of a halogen atom relative to one gram atom of the metal magnesium

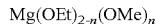
$$Mg(OEt)_{2-n}(OMe)_n \qquad (I)$$

where Et is an ethyl group, Me is a methyl group and n is a numerical value of from 0.001 to 1.

The form and the like of the metal magnesium are not particularly limited. The surface state of the metal magnesium is not also particularly limited but metal magnesium without a coating of magnesium hydroxide or the like on the surface thereof is preferred.

Although the purity and water content of ethanol and methanol, which both ethanol and methanol may be hereinafter abbreviated to alcohol, are not particularly limited, when using an alcohol having high water content, magnesium hydroxide may be formed on the surface of the metal magnesium. Thus an alcohol having a water content of 1% or below, particularly 2,000 ppm or below, is preferably used. Further, morphology improves with decreasing water content, so that an alcohol having a water content of 200 ppm or below is generally preferably.

Although the kind of the halogen is not particularly limited, chlorine, bromine or iodine is preferably used. Iodine is particularly preferably used.

The kind of the halogen-containing compound is not limited, and any compound containing a halogen atom may be used. Although the kind of the halogen atom is not particularly limited, chlorine, bromine or iodine is preferred. Among the halogen-containing compounds, halogen-containing metal compounds are particularly preferred.

As the halogen-containing compound, specifically, $MgCl_2$, $MgI_2$, $Mg(OEt)Cl$, $Mg(OEt)I$, $MgBr_2$, $CaCl_2$, $NaCl$ and $KBr$ are suitably used. Of these, $MgCl_2$ is particularly preferred. The state, shape, granularity and the like of the halogen-containing compound are not particularly limited. For instance, it may be used in the state of a solution in an alcohol solvent (for example, ethanol).

The halogens or the halogen-containing compounds may be used individually or in a combination of two or more halogens or halogen-containing compounds. Further, the halogen and the halogen-containing compound may be used in combination.

The metal magnesium, alcohol and halogen and/or the halogen-containing compound can be reacted in a way similar to known ways except for the use of ethanol and methanol together. That is, they are reacted until no more hydrogen gas is generated, usually for 4 to 30 hours, to obtain a magnesium compound. The reaction may be carried out by either a batch method or a continuous method. The reaction temperature is not particularly limited, but the temperature is preferably 70° C. or more in view of exhibition of activity and control of molecular weight.

Specifically, for example, when using iodine as the halogen, the magnesium compound can be produced by the process of adding iodine in a solid state to a mixture of ethanol, methanol and the metal magnesium and then reacting the result under heating; of adding the alcohol solution of iodine dropwise to the mixture of ethanol, methanol and the metal magnesium and then reacting the result under heating; and of dropwise adding the alcohol solution of iodine to the mixture of ethanol, methanol and the metal magnesium while heating it.

Each method is preferably carried out in the atmosphere of an inert gas (e.g., nitrogen gas or argon gas) and optionally in the presence of an inert organic solvent (e.g., a saturated hydrocarbon such as n-hexane).

Further, it is not required to charge the entire amount of each of the metal magnesium, methanol, ethanol and halogen and/or halogen-containing compound at once from the beginning, and they may be divided and partially charged. In a particularly preferred embodiment, a mixture of ethanol and methanol, and a halogen and/or halogen-containing compound are entirely charged in the beginning, the metal magnesium is divided into several portions and such portions are charged separately. In this embodiment, the generation of a large amount of hydrogen gas can be prevented, which is desirable in view of safety. Further, the size of the reaction vessel can be decreased. Further, it is also made possible to prevent the dissipation of alcohol and halogen caused by the momentary generation of a large amount of hydrogen gas. While the number of the portions can be determined by taking account of the size of the reaction vessel and is not specially limited, suitably, each is generally divided into five to ten portions to avoid complicating the procedures.

Further, there may be employed a variant method in which the entire amount of the halogen and/or halogen-containing compound, ethanol and methanol is charged in the beginning, a small amount of the metal magnesium is added to the alcohol, the product formed by the reaction is removed by separating it into another vessel, a small amount of the metal magnesium is then charged, and these procedures are repeated.

The total amount of ethanol and methanol is used preferably in an amount of from 2 to 100 mole relative to one mole of the metal magnesium, particularly preferably in an amount of from 5 to 50 mole. When the total amount of ethanol and methanol is more than 100 mole, the yield of the magnesium compound having good morphology (particle diameter distribution, shape) may be reduced, and when less than 2 mole, smooth agitation in a reaction vessel may not be possible.

The ratio of methanol to the total amount of ethanol and methanol is properly adjusted so as to satisfy n of the above formula (I). For example, the ratio is preferably 0.05 mol % to 50 mol %, more preferably 0.5 mol % to 20 mol %, particularly preferably 0.5 mol % to 10 mol %

The use amount of the halogen as a halogen atom per mole of the metal magnesium is 0.0001 gram atom or more, preferably 0.0005 gram atom or more, more preferably 0.001 gram atom or more. When the use amount of the halogen is less than 0.0001 gram atom, there is no difference from a case where halogen is used as a reaction initiator, and when the thus-obtained magnesium compound is used as a catalyst support, the catalyst may be poor in catalyst activity or an olefin polymer may be defective in morphology, and the like. Although the upper limit of the use amount of halogen is not particularly limited, the upper limit may be properly selected so long as a desired magnesium compound can be obtained. An upper limit of less than 0.06 gram atom is generally selected.

The use amount of the halogen-containing compound as a halogen atom per mole of the metal magnesium is 0.0001 gram atom or more, preferably 0.0005 gram atom or more, more preferably 0.001 gram atom or more. When the use amount of the halogen-containing compound is less than 0.0001 gram atom, there is no difference from a case where halogen-containing compound is used as a reaction initiator, and when the thus-obtained magnesium compound is used as a catalyst support, the catalyst may be poor in catalyst activity or an olefin polymer may be defective in morphology, and the like. Although the upper limit of the use amount of halogen-containing compound is not particularly limited, the upper limit may be properly selected so long as a desired magnesium compound can be obtained. An upper limit of less than 0.06 gram atom is generally selected.

When both a halogen and a halogen-containing compound are used, the total amount of the halogen atom per mole of the metal magnesium is 0.0001 gram atom or more, preferably 0.0005 gram atom or more, more preferably 0.001 gram atom or more. Although the upper limit of the amount of halogen and/or halogen-containing compound is not particularly limited, the upper limit may be properly selected so long as a desired magnesium compound can be obtained. Generally, an upper limit of less than 0.06 gram atom is preferably selected.

In the invention, the particle diameter of the magnesium compound can freely be controlled by properly selecting the amount of the halogen and/or halogen-containing compound used.

The magnesium compound obtained by the above reaction is solid and substantially magnesium alkoxide represented by the formula (I).

$$Mg(OEt)_{2-n}(OMe)_n \quad (I)$$

Here, the term "substantially" means that not only the case where the support consists purely of the magnesium compound of $Mg(OC_2O_5)_{2-n}(OMe)_n$ but also the case where the support additionally contains infinitesimal impurities (for instance, a case where an alcohol complex of a magnesium halide such as MgI adheres to the support surface, which the plate crystallizations of $Mg(OC_2O_5)_{2-n}(OMe)_n$ aggregate to let to be nearly spherical shape, and the like) are included. In the present invention, even though the impurities are contained, when the purity of $Mg(OC_2O_5)_{2-n}(OMe)_n$ at least 95%, it can be used as the support. Preferred purity is at least 98%, more preferred purity is at least 99%.

The composition of the magnesium compound is preferably in between $Mg(OEt)_{1.999}(OMe)_{0.001}$ and $Mg(OEt)(OMe)$, namely n is preferably 0.001 to 1. In the formula (I), when n does not fall within the range, the nature of the magnesium compound approximates to that of magnesium diethoxide or a magnesium dimethoxide and the advantageous effects of the invention are hardly exhibited, it being undesirable. n is more preferably 0.01 to 0.5, particularly preferably 0.01 to 0.2.

Such a composition enables the preferable composition and form of a solid catalyst component (A) so that the activity significantly increases and chain transfer by hydrogen efficiently proceeds in ethylene polymerization. Polymer powder obtained is generally reflected by the form of support particles. In the composition range, fine plate-like crystals tightly aggregates to form homogenous and spherical support particles. This tendency becomes remarkable at 70° C. or higher.

When using the thus-obtained magnesium compound for the solid catalyst component, the dried compound or the compound washed with an inert solvent such as heptane after filtration may be used. In each case, the magnesium compound used for the invention can be used in the following steps without subjecting it to pulverization or classification for uniformizing the particle size distribution. Further, the magnesium compound has a nearly spherical shape, a sharp particle size distribution and a small sphericity variation among the particles. The magnesium compound may be used individually or in a combination of two kinds or more. Further, it may be used in the state supported on a support such as silica, alumina or polystyrene, and as a mixture with a halogen or the like.

The magnesium compound of the invention preferably has an average particle diameter $D_{50}$ Of from 4 to 20 μm and a particle size distribution index (P) represented by the general formula (I) of P<4.0

$$P=(D_{90}/D_{10}) \quad (1)$$

where $D_{90}$ is a particle diameter corresponding to 90% of cumulative weight fraction, and $D_{10}$ is a particle diameter corresponding to 10% of cumulative weight fraction.

[Solid Catalyst Component]

Next, the solid catalyst component of the invention will be specifically explained.

The solid catalyst component of the invention can be obtained by reacting the above-mentioned magnesium compound (a), titanium compound (b), and if necessary, a halide (c) and/or an electron donating compound (d) and if necessary, a halide (c) and/or an alcohol (e).

Each of the components will be explained below but the explanation of the magnesium compound (a) is omitted since it has been explained above.

(b) Titanium Compound

Although not specially limited, the compound represented by the formula (II) can be preferably used

$$Ti(OR)_qX_{4-q} \quad (II)$$

where X is a halogen atom, R is a hydrocarbon group having from 1 to 10 carbon atoms, q is an integer of from 0 to 4, and a plurality of R's are the same as or different from each other when q is 2 or more.

X denotes a halogen atom, and of halogen atoms, preferred is a chlorine atom or a bromine atom and particularly preferred is a chlorine atom. R denotes a hydrocarbon group, which may be a saturated group or an unsaturated group, which may have a straight chain, branched chain or cyclic structure. As R, an alkyl group, an alkenyl group, a cycloalkenyl group, an aryl group, an aralkyl group and the like are preferred, and a straight chain or branched chain alkyl group is particularly preferred. When a plurality of groups as R are present, they may be the same as, or different from, each other.

Specific examples of R include methyl, ethyl, n-propyl, isopropyl, n-butyl, sec-butyl, isobutyl, n-pentyl, n-hexyl, n-heptyl, n-octyl, n-decyl, allyl, butenyl, cyclopentyl, cyclohexyl, cyclohexenyl, phenyl, tolyl, benzyl and phenethyl.

q is an integer of from 0 to 4.

Specific examples of the halogen-containing titanium compounds of the above-mentioned general formula (II) include tetraalkoxy titanium such as tetramethoxytitanium, tetraethoxytitanium, tetra-n-propoxytitanium, tetraisopropoxytitanium, tetra-n-butoxytitanium, tetraisobutoxytitanium, tetracyclohexyloxytitanium, and tetraphenoxytitanium; titanium tetrahalides such as titanium tetrachloride, titanium tetrabromide and titanium tetraiodide; alkoxytitanium trihalides such as methoxytitanium trichloride, ethoxytitanium trichloride, propoxytitanium trichloride, n-butoxytitanium trichloride and ethoxytitanium tribromide; dialkoxytitanium dihalides such as dimethoxytitanium dichloride, diethoxytitanium dichloride, diisopropoxytitanium dichloride, di-n-propoxytitanium dichloride and diethoxytitanium dibromide; and trialkoxytitanium monohalides such as trimethoxytitanium chloride, triethoxytitanium chloride, triisopropoxytitanium chloride, tri-n-propoxytitanium chloride and tri-n-butoxytitanium chloride.

Of these, high-halogenated titanium compounds are preferred, and titanium tetrachloride is particularly preferred, in view of polymerization activity.

These halogen-containing titanium compounds may be used individually or as a combination of two or more compounds.

(c) Halide

The halide includes silicon tetrachloride, silicon tetrabromide, tin tetrachloride and hydrogen chloride, and of these, silicon tetrachloride is particularly preferred. These halides may be used individually or as a combination of two or more halides.

(d) Electron Donating Compound

The electron donating compound is preferably used since it may improve the stereoregularity of an olefin polymer to be obtained. The electron donating compounds include oxygen-containing electron donors such as alcohols, phenols, ketones, aldehydes, carboxylic acids, malonic acids, succinic acid, esters of organic acids or inorganic acids and ethers such as monoether, diether and polyether, and nitrogen-containing electron donors such as ammonia, amine, nitrile and isocyanate. Of these, esters of polycarboxylic acids are preferred, and esters of aromatic polycarboxylic acids are more preferred. Of these, a monoester and/or a diester of aromatic dicarboxylic acid are/is particularly preferred in view of polymerization activity. Further, the organic groups of the ester portions are preferably a linear, branched or cyclic aliphatic hydrocarbon group.

Specific examples of the electron donating compounds include dialkyl esters such as methyl, ethyl, n-propyl, isopropyl, n-butyl, isobutyl, t-butyl, n-pentyl, 1-methylbutyl, 2-methylbutyl, 3-methylbutyl, 1,1-dimethylpropyl, 1-methylpentyl, 2-methylpentyl, 3-methylpentyl, 4-methylpentyl, 1-ethylbutyl, 2-ethylbutyl, n-hexyl, cyclohexyl, n-heptyl, n-octyl, n-nonyl, 2-methylhexyl, 3-methylhexyl, 4-methylhexyl, 2-ethylhexyl, 3-ethylhexyl, 4-ethylhexyl, 2-methylpentyl, 3-methylpentyl, 2-ethylpentyl or 3-ethylpentyl dicarboxylates such as phthalate, naphthalene-1,2-dicarboxylate, naphthalene-2,3-dicarboxylate, 5,6,7,8-tetrahydronaphthalene-1,2-dicarboxylate, 5,6,7,8-tetrahydronaphthalene-2,3-dicarboxylate, indan-4,5-dicarboxylate and indan-5,6-dicarboxylate.

Of these, phthalic acid diesters are preferred, and phthalic acid diesters in which the organic group of an ester portion is a linear or branched aliphatic hydrocarbon group having 4 or more carbon atoms are particularly preferred.

Preferable specific examples of the phthalic acid diesters include di-n-butyl phthalate, diisobutyl phthalate, di-n-heptyl phthalate and diethyl phthalate and the like. These electron donating compounds may be used individually or as a combination of two or more compounds.

(e) Alcohol

In the invention, if necessary, alcohol (e) is employed. A linear or branched aliphatic alcohol or an aliphatic cyclic alcohol may be employed. Specific examples include methanol, ethanol, propanol, isopropanol, butanol, isobutanol, amylalcohol, octanol, cyclopentanol and cyclohexanol. Of these, isopropanol is particularly preferred.

[Preparation of Solid Catalyst Component]

As a method of preparing the solid catalyst component, the above-mentioned magnesium compound (a) titanium compound (b), and, if necessary, the halide (c) and, if necessary, the electron donating compound (d) or the alcohol (e) may be brought into contact and react with each other. Further, these compounds are preferably brought into contact and react with each other in the amounts thereof under the condition with the operations as follows:

The above-mentioned titanium compound (b) is usually used in an amount within a range of from 0.5 to 100 moles relative to one mole of magnesium of the above-mentioned magnesium compound (a), preferably from 1 to 50 moles.

The above-mentioned halide (c) is usually used in an amount within a range of from 0.01 to 10 moles relative to one mole of magnesium of the magnesium compound (a), preferably from 0.1 to 2 moles.

The above-mentioned electron donating compound (d) is usually used in an amount within a range of from 0.01 to 10 moles relative to one mole of magnesium of the magnesium compound (a), preferably from 0.05 to 0.15 mole.

The above-mentioned alcohol (e) is usually used in an amount within a range of from 0.1 to 1 moles relative to one mole of magnesium of the magnesium compound (a), preferably from 0.2 to 0.8 mole.

The contact temperature is usually within a range of from −20 to 200° C., preferably from 20 to 150° C. The contact period of time is usually from one minute to 24 hours, preferably from 10 minutes to 6 hours.

The procedure of the contact operation is not particularly limited. For instance, the components may be brought into contact with each other in the presence of an inert solvent such as a hydrocarbon, or the components previously diluted with an inert solvent such as a hydrocarbon may be brought into contact with each other. The inert solvent includes aliphatic hydrocarbons such as n-pentane, isopentane, n-hexane, n-heptane, n-octane and isooctane; aromatic hydrocarbons such as benzene, toluene and xylene, and mixtures of these hydrocarbons.

The contact of the titanium compound is preferably carried out two or more times so that the titanium compound is sufficiently supported on the magnesium compound which serves as the catalyst support.

A solid catalyst component obtained by the above contact may be washed with an inert solvent such as a hydrocarbon. The above-mentioned inert solvents may be used.

Further, although the washing method is not particularly limited, methods such as decantation and filtration are preferred. Although the amount of the inert solvent used, washing period of time and number of washing times are also not particularly limited, the solvent is usually used in an amount of from 100 to 100,000 mL, preferably from 1,000 to 50,000 mL relative to one mole of the magnesium compound, and the contact is usually carried out for one minute to 24 hours, preferably for 10 minutes to 6 hours. When the ratio of the solvent is outside the above-mentioned range, the washing may not be completely carried out.

Although pressure at washing time varies depending upon the kind of solvent, the washing temperature and the like, the washing is usually carried out under a pressure within the range of from 0 to 50 kg/cm$^2$ G, preferably from 0 to 10 kg/cm$^2$ G. Further, during the washing operation, stirring is preferably carried out from the viewpoint of the uniformity of washing and the washing efficiency. The solid catalyst component thus obtained can be stored in the dried state, or in an inert solvent such as a hydrocarbon.

As a method of preparing the solid catalyst component (A) useful forethylene-based polymerization, the above-mentioned magnesium compound (a), titanium compound (b), and, if necessary, the halide (c) and, if necessary, the alcohol (e) may be brought into contact and react with each other. Further, these compounds are preferably brought into contact and react with each other in the amounts thereof under the condition with the operations as follows:

When the solid catalyst component is obtained by reacting the magnesium compound and the titanium compound, the magnesium compound is dispersed in an inert solvent. Any inert solvent that is inert to the magnesium compound and the solid catalyst component may be used, for example, various solvents such as aliphatic hydrocarbons, alicyclic hydrocarbons and aromatic hydrocarbons can be used. Specifically preferred are butane, pentane, hexane, heptane, octane cyclohexane, toluene, ethylbenzene and the like. The amount of the magnesium compound is not particularly limited, but it is preferably 50 to 500 g relative to one liter of a solvent in view of handling conveniences.

Next the titanium compound is added to this dispersed system, and then reacted at a temperature of from 0 to 200° C., preferably from 50 to 150° C. with stirring under a pressure of atmospheric pressure or compression. The titanium compound is generally added in a moler amount equal to or more than that of the magnesium compound, preferably 1 to 20 times the moler amount thereof, particularly preferably 1.5 to 10 times the moler amount thereof. The reaction time is generally 5 minutes to 10 hours, preferably 30 minutes to 8 hours, depending on reaction temperature.

When the solid catalyst component is obtained by reacting the magnesium compound, the titanium compound, the halogen compound and, if necessary, the alcohol, the magnesium compound is dispersed in an inert solvent. The above-mentioned inert solvents may be used. Next the halogen compound and, if necessary, the alcohol are reacted with the dispersed system at a certain temperature for a certain period of time under stirring to modify the magnesium compound.

The halogen compound is generally added at a ratio of halogen/magnesium (atom ratio) of 1.5 or less, preferably 0.2 to 1.5, particularly preferably 0.5 to 1.5. If the ratio is out of the range, the activity, hydrogen sensitivity and powder form may be disadvantageously degraded. The alcohol is generally added at a ratio of OH/magnesium (atom ratio) of 0.1 or more. The upper limit thereof is not particularly limited but the use in a large amount is the waste of titanium compound. Thus the upper limit of OH/halogen (atom ratio) is generally 1. In the case where the amount of alcohol used is less than this limit, polymerization activity and apparent density of polymer may not be enhanced.

The reaction temperature is generally 0 to 150° C., preferably 20 to 100° C. The reaction time is generally 5 minutes to 5 hours, preferably 30 minutes to 3 hours, depending on reaction temperature. The contact order of the compounds in the above reaction is not important. For example, the components may be contact with each other in the presence of an inert solvent such as hydrocarbons. Alternatively the components each are diluted with an inert solvent such as hydrocarbons in advance and then contacted.

After modifying the magnesium compound, a titanium compound is further added and reacted with stirring at 0 to 200° C., preferably 50 to 150° C. under a pressure of atmosphere or compression. The titanium compound is generally added in a moler amount equal to or more than that of the magnesium compound, preferably an excessive amount, specifically 1 to 20 times or more the moler amount thereof, particularly preferably 1.5 to 10 times the moler amount thereof. The reaction time is generally 5 minutes to 10 hours, preferably 30 minutes to 8 hours, depending on reaction temperature.

After the above reaction, a solid catalyst component is separated from the reaction product and washed. Any washing solvent that is inert to the solid catalyst component may be used, various solvents such as aliphatic hydrocarbons, alicyclic hydrocarbons and aromatic hydrocarbons can be used. Specifically preferred are butane, pentane, hexane, heptane, octane cyclohexane, toluene, ethylbenzene and the like. Further, although the washing method is not particularly limited, methods such as decantation and filtration are preferred. Although the amount of the inert solvent used, washing period of time and number of washing times are also not particularly limited, the solvent is usually used in an amount of from 100 to 100,000 mL, preferably from 1,000 to 50,000 mL relative to one mole of the magnesium compound, and the contact is usually carried out for one minute to 24 hours, preferably for 10 minutes to 6 hours. When the ratio of the solvent is outside the above-mentioned range, the washing may not be completely carried out. Although pressure at washing time varies depending upon the kind of solvent, the washing temperature and the like, the washing is usually carried out under a pressure within the range of from 0 to 50 kg/cm$^2$G, preferably from 0 to 10 kg/cm$^2$G. Further, during the washing operation, stirring is preferably carried out from the viewpoint of the uniformity of washing and the washing efficiency. The solid catalyst component thus obtained can be stored in the dried state, or in an inert solvent such as hydrocarbons.

[Catalyst for Olefin Polymerization]

The catalyst for olefin polymerization of the invention include the solid catalyst component (A), organometallic compound (B), and, if necessary, the electron donating compound (C).

Each of the components will be explained below, but the explanation of the solid catalyst component (A) is omitted since it has been explained above.

(B) Organometallic Compound

As the organometallic compound for the invention, for example, an organoaluminum compound can be used. Although not specially limited, the organoaluminum compound can be preferably selected from an organoaluminum compound having an alkyl group, a halogen atom, a hydrogen atom and an alkoxy group, aluminoxane, or a mixture of these. Specific examples thereof include trialkylaluminum compounds such as trimethylaluminum, triethylaluminum, triisopropylaluminum, triisobutylaluminum and trioctylaluminum; dialkylaluminum monochlorides such as diethylaluminum monochloride, diisopropylaluminum monochloride, diisobutylaluminum monochloride and dioctylaluminum monochloride; alkylaluminum sesquihalides such as ethylaluminum sesquichloride; and linear aluminoxanes such as methylaluminoxane.

Of these organoaluminum compounds, trialkylaluminum having a lower alkyl group having 1 to 5 carbon atoms is preferred, and trimethylaluminum, triethylaluminum, tripropylaluminum and triisobutylaluminum are particularly preferred.

These organoaluminum compounds may be used solely, or two or more thereof may be used in combination.

(C) Electron Donating Compound

In the invention, the electron donating compound is preferably used since it may improve the stereoregularity of an olefin polymer to be obtained.

As the electron donating compound, organosilicon compounds having an alkoxy group, nitrogen-containing compounds, phosphorous-containing compounds and oxygen-containing compounds may be used. Of these, it is particularly preferred to use an organosilicon compound having an alkoxy group.

Specific examples of the organosilicon compound having an alkoxy group include trimethylmethoxysilane, trimethylethoxysilane, triethylmethoxysilane, triethylethoxysilane, dimethyldimethoxysilane, dimethyldiethoxysilane, ethylisopropyldimethoxysilane, propylisopropyldimethoxysilane, diisopropyldimethoxysilane, diisobutyldimethoxysilane, isopropylisobutyldimethoxysilane, di-t-butyldimethoxysilane, t-butylmethyldimethoxysilane, t-butylethyldimethoxysilane, t-butylpropyldimethoxysilane, t-butylisopropyldimethoxysilane, t-butylbutyldimethoxysilane, t-butylisobutyldimethoxysilane, t-butyl(s-butyl)dimethoxysilane, t-butylamyldimethoxysilane, t-butylhexyldimethoxysilane, t-butylheptyldimethoxysilane, t-butyloctyldimethoxysilane, t-butylnonyldimethoxysilane, t-butyldecyldimethoxysilane, t-butyl(3,3,3-trifluoromethylpropyl)dimethoxysilane, cyclohexylmethyldimethoxysilane, cyclohexylethyldimethoxysilane, cyclohexylpropyldimethoxysilane, cyclohexylisobutyldimethoxysilane, dicyclohexyldimethoxysilane, cyclohexyl-t-butyldimethoxysilane, cyclopentylmethyldimethoxysilane, cyclopentylethyldimethoxysilane, cyclopentylpropyldimethoxysilane, cyclopentyl-t-butyldimethoxysilane, dicyclopentyldimethoxysilane, cyclopentylcyclohexyldimethoxysilane, bis(2-methylcyclopentyl)dimethoxysilane, bis(2,3-dimethylcyclopentyl)dimethoxysilane, α-naphthyl-1,1,2-trimethylpropyldimethoxysilane, n-tetradecanyl-1,1,2-trimethylpropyldimethoxysilane, 1,1,2-trimethylpropylmethyldimethoxysilane, 1,1,2-trimethylpropylethyldimethoxysilane, 1,1,2-trimethylpropylisopropyldimethoxysilane, 1,1,2-trimethylpropylcyclopentyldimethoxysilane, 1,1,2-trimethylpropylcyclohexyldimethoxysilane, 1,1,2-trimethylpropylmyristyldimethoxysilane, diphenyldimethoxysilane, diphenyldiethoxysilane, phenyltriethoxysilane, methyltrimethoxysilane, methyltriethoxysilane, ethyltrimethoxysilane, ethyltriethoxysilane, propyltrimethoxysilane, isopropyltrimethoxysilane, butyltrimethoxysilane, butyltriethoxysilane, isobutyltrimethoxysilane, t-butyltrimethoxysilane, s-butyltrimethoxysilane, amyltrimethoxysilane, isoamyltrimethoxysilane, cyclopentyltrimethoxysilane, cyclohexyltrimethoxysilane, norbornanetrimethoxysilane, indenyltrimethoxysilane, 2-methylcyclopentyltrimethoxysilane, ethyltriisopropoxysilane, methylcyclopentyl(t-butoxy)dimethoxysilane, isopropyl(t-butoxy)dimethoxysilane, t-butyl(t-butoxy)dimethoxysilane, (isobutoxy)dimethoxysilane, vinyltriethoxysilane, vinyltributoxysilane, chlorotriethoxysilane, γ-chloropropyltrimethoxysilane, γ-aminopropyltriethoxysilane, 1,1,2-trimethylpropyltrimethoxysilane, 1,1,2-trimethylpropylisopropoxydimethoxysilane, 1,1,2-trimethylpropyl(t-butoxy)dimethoxysilane, tetramethoxysilane, tetraethoxysilane, tetrabutoxysilane, tetraisobutoxysilane, ethyl silicate, butyl silicate, trimethylphenoxysilane, methyltriallyloxysilane, vinyltris(β-methoxyethoxy)silane, vinyltrisacetoxysilane and dimethyltetraethoxydisiloxane and the like. These organosilicon compounds may be used solely each, or two or more thereof may be used in combination.

The above organosilicon compound having an alkoxy group also includes a compound obtained by reacting a silicon compound having no Si—O—C bond with an organic compound having an O—C bond in advance or by reacting these compounds during the polymerization of an olefin to obtain an organosilicon compound having a Si—O—C bond. Specifically, a compound obtained by reacting silicon tetrachloride and an alcohol is included.

Specific examples of the nitrogen-containing compound include 2,6-substituted piperidines such as 2,6-diisopropylpiperidine, 2,6-diisopropyl-4-methylpiperidine and N-methyl-2,2,6,6-tetramethylpiperidine; 2,5-substituted azolidines such as 2,5-diisopropylazolidine and N-methyl-2,2,5,5-tetramethylazolidine; substituted methylenediamines such as N,N,N',N'-tetramethylmethylenediamine and N,N,N',N'-tetraethylmethylenediamine; and substituted imidazolidines such as 1,3-dibenzylimidazolidine and 1,3-dibenzyl-2-phenylimidazolidine.

Specific examples of the phosphorus-containing compound include phosphorous acid esters such as triethyl phosphite, tri-n-propyl phosphite, triisopropyl phosphite, tri-n-butyl phosphite, triisobutyl phosphite, diethyl-n-butyl phosphite and diethylphenyl phosphite.

Specific examples of the oxygen-containing compound include 2,5-substituted tetrahydrofurans such as 2,2,5,5-tetramethyltetrahydrofuran and 2,2,5,5-tetraethyltetrahydrofuran; and 2,6-substituted tetrahydrofurans such as 2,2,6,6-tetramethyltetrahydrofuran and 2,2,6,6-tetraethyltetrahydrofuran; and dimethoxymethane derivatives such as 1,1-dimethoxy-2,3,4,5-tetrachlorocyclopentadiene, 9,9-dimethoxyfluorene and diphenyldimethoxymethane.

Although the amount of each component of the catalyst in the present invention is not especially limited, the solid catalyst component (A) is used in such an amount that the titanium atom amount per liter of a reaction volume is generally in the range of 0.00005 to 1 mmol.

The organometallic compound (B) is used in such an amount that the metal/titanium atomic ratio is generally in the range of from 1 to 1000, preferably from 10 to 500. When the above atomic ratio is outside the above-mentioned range, the catalyst activity is sometimes insufficient.

Further, when the electron donating compound (C) is used, the electron donating compound (C) is used in such an amount that the electron donating compound (C)/the organometallic compound (B) molar ratio is generally in the range of from 0.001 to 5.0, preferably from 0.01 to 2.0, more preferably from 0.05 to 1.0. When the above molar ratio is outside the above range, the sufficient catalyst activity and the stereoregularity sometimes cannot be obtained. When a preliminary polymerization is carried out, however, the amount of the electron donating compound (C) can be further decreased.

[Method of Producing Polyolefin]

In the method of producing polyolefin of the invention, an olefin is polymerized by using the above-mentioned catalyst for olefin polymerization.

The olefin used in the invention is preferably the α-olefin represented by the following formula (III):

$$R^1-CH=CH_2 \quad (III)$$

In the general formula (III), $R^1$ is a hydrogen atom or a hydrocarbon and the hydrocarbon group may be saturated or unsaturated, may be linear or branched, or may be cyclic.

Specific examples of the α-olefin include ethylene, propylene, 1-butene, 1-pentene, 1-hexene, 1-heptene, 1-octene, 1-decene, 3-methyl-1-pentene, 4-methyl-1-pentene, vinylcyclohexane, butadiene, isoprene, piperylene, and the like. These olefins may be used solely each, or two or more thereof may be used in combination. Among olefins, ethylene and propylene are particularly preferred.

The polymerization type of the olefin polymerization is not especially limited, and any one of solution polymerization, slurry polymerization, gas phase polymerization, bulk polymerization, etc. can be employed. Further, any one of a batch polymerization and a continuous polymerization can be employed, and there can be employed two-step polymerization or multi-step polymerization that is carried out under different conditions.

The reaction condition is not especially limited, the polymerization pressure therefor is optionally selected within a pressure range of generally from atmospheric pressure to 8 MPa, preferably from 0.2 to 5 MPa, and the polymerization temperature is optionally selected within a temperature range of generally from 0 to 200° C., preferably from 30 to 100° C. Although the polymerization time period varies depending upon the kind of olefins or the polymerization temperature so that it cannot be categorically determined, it is generally from 5 minutes to 20 hours, preferably approximately from 10 minutes to 10 hours.

In the polymerization of an olefin in the invention, the preliminary polymerization of an olefin may be carried out as required before the regular polymerization thereof in view of the polymerization activity, the stereoregularity and powder form of the olefin polymer. In this case, the preliminary polymerization of the olefin is carried out in the presence of a catalyst that is a mixture of predetermined amounts of the solid catalyst component (A), the organometallic compound (B) and optionally the electron donating compound (C), generally in the temperature range of from 0 to 100° C. under a pressure of from atmospheric pressure to approximately 5 MPa, and then the regular polymerization of the olefin is carried out in the presence of the catalyst and the preliminary polymerization product.

The molecular weight of the polyolefin can be adjusted by the addition of a chain transfer agent, preferably the addition of hydrogen. Further, an inert gas such as nitrogen may be present. Alternatively, after the catalyst components (A), (B) and (C) used in the invention are mixed in the predetermined ratio and brought into contact, an olefin may be polymerized at once, or the catalyst components are subjected to maturation for approximately from 0.2 to 3 hours after contact operation, then, an olefin may be polymerized. Further, the catalyst components can be supplied in the state of a suspension in an inert solvent, an olefin or the like.

In the invention, after-treatment of polymerization can be carried out with common procedures. Namely, in the gas phase polymerization, nitrogen gas stream may be passed through the polymer powder taken from the polymerization vessel after polymerization to remove olefins therein, or, if necessary, the polymer may be pelletized with an extruder, and in this regard, a small amount of water, an alcohol or the like may be added in order to completely deactivate the catalyst. In the bulk polymerization, the monomers may be completely separated from the polymer taken from the polymerization vessel after polymerization, followed by pelletizing of the polymer.

[Ethylene Polymerization]

Specifically, the above-mentioned solid catalyst component (A) and organoaluminum (B) are added to a polymerization system as catalyst components. Then, ethylene, or ethylene and α-olefin is introduced. The α-olefin used in ethylene copolymerization is represented by the following formula (IV):

$$R^2-CH=CH_2 \quad (IV)$$

$R^2$ is a hydrocarbon and the hydrocarbon group may be saturated or unsaturated, may be linear or branched, or may be cyclic. Specific examples of the α-olefin include propylene, 1-butene, 1-pentene, 1-hexene, 1-heptene, 1-octene, 1-decene, 3-methyl-1-pentene, 4-methyl-1-pentene, vinylcyclohexane, butadiene, isoprene, piperylene, and the like. Among olefins, 1-butene, 1-pentene, 1-hexene, 1-heptene, 1-octene and 1-decene are preferred. These olefins may be used solely each, or two or more thereof may be used in combination. The amount of α-olefin is usually introduced in an amount within a range of from 0.2 to 5 wt % relative to ethylene.

The polymerization type of the olefin polymerization is not especially limited, and any one of solution polymerization, suspension polymerization and gas phase polymerization can be employed. Further, any one of a batch polymerization and a continuous polymerization can be employed, and there can be employed two-step polymerization or multi-step polymerization that is carried out under different conditions.

The amount of the catalyst component is not particularly limited, when solution polymerization or suspension polymerization is employed, the solid catalyst component (A) is used in such an amount that the titanium atom amount per liter of a reaction volume is generally in the range of 0.00005 to 1 mmole. The organoaluminum compound (B) is used in such an amount that the aluminum/titanium atomic ratio is generally in the range of from 5 to 1,000, preferably from 15 to 200. Alternatively, after the catalyst components (A) and (B) used in the invention are mixed in the predetermined ratio and brought into contact, ethylene and an olefin may be polymerized at once, or the catalyst components are subjected to maturation for approximately from 0.2 to 3 hours after contact operation, then, ethylene and an olefin may be polymerized. The ethylene pressure of reaction system is generally from atmospheric pressure to 10 MPa, preferably from 0.5 to 5 MPa. The reaction temperature is generally from 20 to 200° C., preferably from 50 to 150° C. The reaction time is generally from 5 minutes to 10 hours, preferably from 30 minutes to 5 hours. Although the molecular weight can be controlled by polymerization conditions including a polymerization temperature, concentration of catalyst and molar ratio of catalyst, it is effectively controlled in the presence of hydrogen.

EXAMPLES

The invention will be specifically explained with reference to Examples, while the invention shall not be limited to Examples.

The magnesium compound and polyolefin obtained in examples were evaluated according to the following methods.

(1) Sphericity (S) of Magnesium Compound

A photograph of a dried magnesium compound was taken using a scanning electron microscope (trade name: JSM-25SIII, product of JEOL) of 150 magnifications at an acceleration voltage of 5 KV, to obtain a negative. Then, the negative was image-processed by a transmission method. Particles equivalent to 20 pixels (one pixel covering a 1.389 μm×1.389 μm area) or smaller in area were cut, and the image processing was carried out with an image analyzer (Nexsus Co., Ltd.) with respect to approximately 2,000 particles remaining. The longest diameter $L_1$ of a projection view of a magnesium compound particle and the diameter $L_2$ of a circle which had an area equal to the projection area of the magnesium compound particle were determined, and the sphericity was calculated on the basis of the following expression (1).

$$S=(L_1/L_2)^3 \quad (1)$$

(2) Particle Size Distribution Index (P) of Magnesium Compound

A magnesium compound was suspended in a hydrocarbon, and in this state, the magnesium compound was measured for particle diameters by a light transmitting method. A particle diameter distribution determined by the measurement was plotted on a logarithmic normal probability paper, and a 50% particle diameter was taken as an average particle diameter ($D_{50}$). A 90% particle diameter ($D_{90}$) and a 10% particle diameter ($D_{10}$) were also taken and the particle size distribution index was then calculated on the basis of the following expression (2).

$$P=(D_{90}/D_{10}) \quad (2)$$

(3) Sphericity (S') of Polymer Powder

The sphericity was calculated as in the case of the magnesium compound.

(4) Particle Size Distribution Index (P') of Polymer Powder

The particle diameter distribution of polymer powder measured with sieves was plotted on a logarithmic normal probability paper, and a 50% particle diameter was taken as an average particle diameter ($D_{50}'$). A 90% particle diameter ($D_{90}'$) and a 10% particle diameter ($D_{10}'$) were also taken and the particle size distribution index was then calculated as in the case of the magnesium compound.

(5) Isotacticity [mmmm]

A polymer was dissolved in 1,2,4-trichlorobenzene, and isotacticity was determined on the basis of signals of methyl measured at 130° C. by a proton complete decoupling method using a $^{13}$C-NMR (trade name: EX-400, product of JEOL).

An isotactic pentad fraction [mmmm] refers to an isotactic fraction in pentad units of a polypropylene molecule chain determined on the basis of the $^{13}$C-NMR spectrum as proposed by A. Zambelli, et al. on page 925 of the Macromolecules, Vol. 6 (1973).

Further, the method of assignment of peaks of $^{13}$C-NMR spectrum was according to the assignment proposed by A. Zambelli, et al. on page 687 of the Macromolecules, Vol. 8 (1975).

(6) Apparent Density (AD)

Measured according to JIS K6721.

(7) Activity

Activity was defined as a value (kg/g-Cat) calculated by dividing the amount of polypropylene obtained in a certain slurry polymerization method by the amount of a solid catalyst component used.

(8) n of $Mg(OEt)_{2-n}(OMe)_n$

A 1.2N hydrochloric acid aqueous solution was added to a sample, the mixture was stirred at room temperature for 24 hours to decompose the sample, and a corresponding alcohol amount was quantitatively determined by gas chromatography to determine n.

(9) Fish Eye

A polymer obtained was dried and thereto were added additives (Irganox 1010: 360 ppm, Irgafos 168: 900 ppm and calcium stearate: 2400 ppm (Chiba Specialty Chemicals.), and DHT-4A: 200 ppm (Kyowa Chemical Industry Co., Ltd.)). The mixture was pelletized with a 20φ uniaxial pelletizer at a molding temperature of 180 to 190° C. and then formed to a film with a 20φ uniaxial inflation molding machine at a molding temperature of 185 to 195° C. (thickness: 6 μm, blow ratio: 1.5). Three films of 10×10 cm were obtained as samples from the film and the total number of fish eyes were visually counted for evaluation.

(10) Melt Index (MI) (g/10 minutes)

Measured at a temperature of 190° C. under a load of 2,160 g according to JIS K7210.

Example 1

(1) Preparation of Magnesium Compound

A three-necked flask having an internal volume of 0.5 liter and having a stirrer was flushed with nitrogen, and 229 ml (3.90 mole) of dehydrated ethanol (EtOH), 2.0 ml (49 mmole) of methanol, 1.2 g (9.5 milligram atom) of iodine and 12 g (0.49 gram atom) of metal magnesium were poured into the three-necked flask and allowed to react at 78° C. with stirring (350 rpm) until no more hydrogen was generated from the system, to give a magnesium compound.

(2) Preparation of Solid Catalyst Component

A three-necked flask having an internal volume of 0.5 liter and equipped with a stirrer was flushed with nitrogen, and 16 g of the magnesium compound obtained in the above (1) and 80 ml of dehydrated octane were placed in the three-necked flask. The mixture was heated to 40° C., and 2.4 ml (23 mmole) of silicon tetrachloride was added. The mixture was stirred for 20 minutes and then added with 3.4 ml (13 mmole) of di-n-butyl phthalate. The resultant solution was temperature-increased up to 80° C., and 77 ml (0.70 mole) of titanium tetrachloride was dropwise added with a dropping funnel. The internal temperature was adjusted to 125° C., and the mixture was stirred for 1 hour, which was defined as a first supporting operation. Then, the reaction product was fully washed with dehydrated octane. Further, 122 ml (1.11 mole) of titanium tetrachloride was added, the internal temperature was adjusted to 125° C., and the mixture was stirred for 2 hours, which was defined as a second supporting operation. Then, the reaction mixture was fully washed with dehydrated octane, to give a solid catalyst component.

(3) Polymerization of Polyolefin

Slurry polymerization was carried out by using propylene as an olefin.

An autoclave made of stainless steel having an internal volume of 1 liter and equipped with a stirrer was fully dried and flushed with nitrogen, and 400 ml of dehydrated heptane was placed therein. Further, 2.0 mmole of triethylaluminum was added, then, 0.25 mmole of dicyclopentyldimethoxysilane was added, and the solid catalyst component prepared in the above (2) was added in an amount of 0.0025 mmole per Ti. Hydrogen was introduced up to 0.1 MPa, and then propylene was introduced. Polymerization was carried out for 1 hour at a total pressure of 0.8 MPa and a temperature of 80° C. Then, the temperature was decreased, the pressure was decreased, and the reaction product was taken out and poured into 2 liters of methanol and vacuum-dried to give polypropylene.

For Example 1, and examples and comparative examples described later, Table 1 shows amounts of materials and reaction conditions for preparing a magnesium compound, and evaluation results on the form of compounds obtained. Table 1 also shows the properties of catalysts and evaluation of propylene obtained.

TABLE 1

|  |  |  | unit | Ex. 1 | Ex. 2 | Ex. 3 | Ex. 4 | Ex. 5 | Ex. 6 |
|---|---|---|---|---|---|---|---|---|---|
| Magnesium Compound | Reaction Condition | Amount of ethanol | (molar ratio) | 7.90 | 7.90 | 7.90 | 7.75 | 7.50 | 7.00 |
|  |  | Amount of methanol | (molar ratio) | 0.10 | 0.10 | 0.10 | 0.25 | 0.50 | 1.00 |
|  |  | Amount of butanol | (molar ratio) | 0.00 | 0.00 | 0.00 | 0.00 | 0.00 | 0.00 |
|  |  | Kind of halogen source |  | $I_2$ | $MgCl_2$ | $I_2$ | $I_2$ | $I_2$ | $I_2$ |
|  |  | Amount of halogen source | (g atom ratio) | 0.019 | 0.019 | 0.0057 | 0.019 | 0.019 | 0.019 |
|  |  | Reaction Temperature | (° C.) | 78 | 78 | 50 | 78 | 78 | 78 |
|  |  | Rotation Number | (rpm) | 350 | 350 | 525 | 350 | 350 | 350 |
|  |  | Pulverization |  | No | No | No | No | No | No |
|  | Evaluation | n |  | 0.02 | 0.02 | 0.02 | 0.05 | 0.13 | 0.34 |
|  |  | 50% Particle Diameter ($D_{50}$) | (μm) | 61 | 59 | 33 | 53 | 50 | 51 |
|  |  | Sphericity (S) |  | 1.30 | 1.32 | 1.29 | 1.28 | 1.31 | 1.30 |
|  |  | Particle Size Distribution Index (P) |  | 3.7 | 3.8 | 3.5 | 3.5 | 3.5 | 3.7 |
| Evaluation of PP Polymerization |  | Activity | (kg/g-Cat) | 20.3 | 20.8 | 34.9 | 40.5 | 16.1 | 14.8 |
|  |  | Stereoregularity | (mol %) | 98.3 | 98.2 | 98.3 | 98.4 | 98.2 | 98.3 |
|  |  | 50% Particle Diameter ($D_{50}'$) | (μm) | 1580 | 1530 | 1080 | 1610 | 1250 | 1100 |
|  |  | Apparent Density (AD) | (g/ml) | 0.35 | 0.36 | 0.41 | 0.38 | 0.39 | 0.41 |
|  |  | Sphericity (S') |  | 1.31 | 1.33 | 1.31 | 1.30 | 1.30 | 1.31 |
|  |  | Particle Size Distribution Index (P') |  | 3.8 | 3.9 | 3.6 | 3.7 | 3.6 | 3.8 |
| Evaluation of PE Polymerization |  | 1st activity | (kg/g-Cat) |  |  |  |  |  |  |
|  |  | 1st MI | (g/10 min) |  |  |  |  |  |  |
|  |  | Fish eye |  |  |  |  |  |  |  |
|  |  | 50% Particle Diameter ($D_{50}'$) | (μm) |  |  |  |  |  |  |
|  |  | Apparent Density (AD) | (g/ml) |  |  |  |  |  |  |
|  |  | Sphericity (S') |  |  |  |  |  |  |  |
|  |  | Particle Size Distribution Index (P') |  |  |  |  |  |  |  |

|  |  |  | unit | Ex. 7 | Comp. Ex. 1 | Comp. Ex. 2 | Comp. Ex. 3 |
|---|---|---|---|---|---|---|---|
| Magnesium Compound | Reaction Condition | Amount of ethanol | (molar ratio) | 7.75 | 8.00 | 0.00 | 8.00 |
|  |  | Amount of methanol | (molar ratio) | 0.25 | 0.00 | 8.00 | 0.00 |
|  |  | Amount of butanol | (molar ratio) | 0.00 | 0.00 | 0.00 | 0.00 |
|  |  | Kind of halogen source |  | $I_2$ | $I_2$ | $I_2$ | $I_2$ |
|  |  | Amount of halogen source | (g atom ratio) | 0.0019 | 0.019 | 0.019 | 0.010 |
|  |  | Reaction Temperature | (° C.) | 78 | 78 | 78 | 78 |
|  |  | Rotation Number | (rpm) | 1500 | 350 | 350 | 330 |
|  |  | Pulverization |  | No | No | No | Yes |
|  | Evaluation | n |  | 0.05 | 0.00 | 2.00 | 0.00 |
|  |  | 50% Particle Diameter ($D_{50}$) | (μm) | 5.5 | 63 | 45 | 5.8 |
|  |  | Sphericity (S) |  | 1.45 | 1.30 | 1.80 | 5.88 |
|  |  | Particle Size Distribution Index (P) |  | 2.9 | 3.8 | 6.8 | 4.3 |
| Evaluation of PP Polymerization |  | Activity | (kg/g-Cat) |  | 14.0 | 3.9 |  |
|  |  | Stereoregularity | (mol %) |  | 98.2 | 98.1 |  |
|  |  | 50% Particle Diameter ($D_{50}'$) | (μm) |  | 1310 | 760 |  |
|  |  | Apparent Density (AD) | (g/ml) |  | 0.31 | 0.28 |  |
|  |  | Sphericity (S') |  |  | 1.31 | 1.85 |  |
|  |  | Particle Size Distribution Index (P') |  |  | 4.1 | 9.8 |  |
| Evaluation of PE Polymerization |  | 1st activity | (kg/g-Cat) | 66.8 |  |  | 39.8 |
|  |  | 1st MI | (g/10 min) | 4400 |  |  | 4000 |
|  |  | Fish eye |  | 65 |  |  | 80 |
|  |  | 50% Particle Diameter ($D_{50}'$) | (μm) | 200 |  |  | 180 |
|  |  | Apparent Density (AD) | (g/ml) | 0.37 |  |  | 0.28 |
|  |  | Sphericity (S') |  | 1.44 |  |  | 5.75 |
|  |  | Particle Size Distribution Index (P') |  | 2.5 |  |  | 3.8 |

In the table, the amount of ethanol and methanol represents a molar ratio relative to metal magnesium (ethanol or methanol/Mg).

The amount of a halogen source (halogen or halogen-containing compound) represents a gram atom ratio relative to metal magnesium (halogen source/Mg).

n represent the value of n of the formula (I).

Example 2

In the preparation of magnesium compound, Example 1 was repeated except that the iodine was replaced with 0.45 g (9.5 milligram atom) of anhydrous magnesium chloride.

Example 3

In the preparation of magnesium compound, Example 1 was repeated except that the amount of iodine was changed to 0.36 g (2.8 milligram atom) and the reaction was carried out at 50° C. with stirring (525 rpm).

Example 4

In the preparation of magnesium compound, Example 1 was repeated except that the amount of ethanol was changed to 225 ml (3.83 mol) and the amount of methanol changed to 5.0 ml (0.12 mol).

Example 5

In the preparation of magnesium compound, Example 1 was repeated except that the amount of ethanol was changed to 217 ml (3.70 mol) and the amount of methanol changed to 10 ml (0.25 mol).

Example 6

In the preparation of magnesium compound, Example 1 was repeated except that the amount of ethanol was changed to 203 ml (3.46 mol) and the amount of methanol changed to 20 ml (0.49 mol).

Example 7

(1) Preparation of Magnesium Compound

A reactor with max blend wing having an internal volume of 1 liter was flushed with nitrogen, and 675 ml (11.5 mole) of dehydrated ethanol (EtOH), 15 ml (0.36 mole) of methanol, 0.36 g (2.9 milligram atom) of iodine and 36.0 g (1.48 milligram atom) of metal magnesium were poured into the reactor with max blend wing and allowed to react at 78° C. with stirring (1500 rpm) until no more hydrogen was generated from the system, to give a magnesium compound.

(2) Preparation of Solid Catalyst Component

A three-necked flask having an internal volume of liter and equipped with a stirrer was flushed with nitrogen, and 15 g (131 mmol) of the magnesium compound obtained in the above (1) and 350 ml of dehydrated hexane were placed in the three-necked flask. Under stirring, 4.9 ml (43 mmol) of silicon tetrachloride and 4.9 ml (64 mmol) of isopropanol were added thereto and allowed to react at 70° C. for 2 hours. Further 36 ml (0.33 mol) of titanium tetrachloride was added and allowed to react at 70° C. for 6 hours. Then, the reaction mixture was washed with hexane to give a solid catalyst component.

(3) Polymerization of Ethylene

An autoclave made of stainless steel having an internal volume of 7 liter and equipped with a stirrer was fully dried and flushed with nitrogen, and 2.5 l of dehydrated hexane was placed therein. Further, 2.5 mmole of triethylaluminum was added and the solid catalyst component prepared in the above (2) was added in an amount of 0.25 mmole in terms of Ti atom. Hydrogen was introduced up to 0.3 MPa, and then ethylene was continuously introduced so as to attain a total pressure of 0.55 MPa. Polymerization was carried out at 85° C. for 60 minutes under stirring. Then, the temperature was lowered to 40° C.

Next after adding 2.5 l of dehydrated hexane, 0.0001 MPa of hydrogen and 20 g of 1-butene were introduced and ethylene was then introduced so as to attain the total pressure of 0.33 MPa. Polymerization was carried out at 80° C. for 30 minutes under stirring. The results are shown in Table 1.

In the table, the first activity is the activity of the first step polymerization and the first MI is the MI of polymer obtained at the first step.

Comparative Example 1

In the preparation of magnesium compound, Example 1 was repeated except that no methanol was added and the amount of ethanol was changed to 232 ml (3.95 mol)

Comparative Example 2

In the preparation of magnesium compound, Example 1 was repeated except that no ethanol was added and the amount of methanol was changed to 160 ml (3.95 mol).

Comparative Example 3

(1) Preparation of Magnesium Compound

A reactor with max blend wing having an internal volume of 1 liter was flushed with nitrogen, and 695 ml (11.8 mole) of dehydrated ethanol (EtOH), 1.8 g (14 milligram atom) of iodine and 36.0 g (1.48 milligram atom) of metal magnesium were poured into the reactor with max blend wing and allowed to react at a reflux temperature (78° C.) with stirring (330 rpm) until no more hydrogen was generated from the system, to give a solid product. 25 g of the fully dried solid product and 200 ml of hexane were placed in a ball mill with an internal volume of 400 ml and 100 balls made of stainless steel having a diameter of 1.2 cm. They were then pulverized for ten hours to give a magnesium compound.

(2) Preparation of Solid Catalyst Component

Example 6(2) was repeated except that the magnesium compound prepared in the above (1) was used.

(3) Polymerization of Ethylene

Example 6(3) was repeated except that the solid catalyst prepared in the above (2) was used. Table 1 shows the results.

INDUSTRIAL UTILITY

The polymerization of an olefin with the catalyst for olefin polymerization obtained using the magnesium compound of the invention provides a polyolefin with high activity, excellently controlled molecular weight, and excellent apparent density and form.

The invention claimed is:

1. A method of producing a magnesium compound represented by formula (I):

$$Mg(OEt)_{2-n}(OMe)_n \qquad (I)$$

where Et is an ethyl group, Me is a methyl group and n is a numerical value of from 0.001 to 1, comprising simultaneously reacting metal magnesium, ethanol, methanol and a halogen and/or a halogen-containing compound comprising at least 0.0001 gram atom of a halogen atom relative to one gram atom of the metal magnesium, wherein the magnesium compound has an average particle diameter D50 of from 4 to 20 μm and a particle size distribution index (P) represented by the formula (1) of P<4.0

$$P=(D90/D10) \quad (1)$$

where D90 is a particle diameter corresponding to 90% of cumulative weight fraction, and D10 is a particle diameter corresponding to 10% of cumulative weight fraction.

2. The method according to claim 1, wherein the magnesium compound has an average particle diameter D50 of from 4 to 20 μm and a particle size distribution index (P) represented by the formula (1) of P<3.8.

3. The method according to claim 1, wherein the halogen is iodine.

4. The method according to claim 1, comprising reacting metal magnesium, ethanol, methanol and a halogen-containing compound, wherein the halogen-containing compound is magnesium dichloride.

5. The method according to claim 1, wherein n of the formula (I) is a numerical value of from 0.01 to 0.2.

6. The method according to claim 1, wherein the ethanol and methanol have a water content of 200 ppm or below, the halogen is chlorine, bromine or iodine, and the halogen-containing compound is MgCl2, MgI2, Mg(OEt)Cl, Mg(OEt)I, MgBr2, CaCl2, NaCl or KBr.

7. The method according to claim 1, wherein the total amount of ethanol and methanol is 5 to 50 mole relative to one mole of the metal magnesium, the ratio of methanol to the total amount of ethanol and methanol is 0.5 mol % to 10 mol %, the amount of the halogen as a halogen atom per mole of the metal magnesium is 0.001 to less than 0.06 gram atom, the amount of the halogen-containing compound as a halogen atom per mole of the metal magnesium is 0.001 to less than 0.06 gram atom, and when both a halogen and a halogen-containing compound are used the total amount of the halogen atom per mole of the metal magnesium is 0.001 to less than 0.06 gram atom.

8. The method according to claim 1, wherein n is 0.01 to 0.5.

9. The method according to claim 7, wherein n is 0.01 to 0.2.

10. The method according to claim 9, wherein the magnesium compound has and a particle size distribution index (P) represented by the general formula (1) of P<3.8.

11. A method of producing a solid catalyst component, comprising reacting the following components (a), (b) and (c'), or components (a), (b), (c') and (d):

(a) a magnesium compound represented by formula (I):

$$Mg(OEt)_{2-n}(OMe)_n \quad (I)$$

where Et is an ethyl group, Me is a methyl group and n is a numerical value of from 0.001 to 1

(b) a titanium compound represented by the formula (II)

$$Ti(OR)_qX_{4-q} \quad (II)$$

where X is a halogen atom, R is a hydrocarbon group having from 1 to 10 carbon atoms, q is an integer of from 0 to 4, and a plurality of R's are the same as or different from each other when q is 2 or more, (c') silicon tetrachloride (d) an electron donating compound, wherein the compound represented by formula (I) is prepared by simultaneously reacting metal magnesium, ethanol, methanol and a halogen and/or a halogen-containing compound comprising at least 0.0001 gram atom of a halogen atom relative to one gram atom of the metal magnesium.

12. A method of producing a solid catalyst component, comprising reacting the following components (a), (b), (c) and (e), or components (a), (b) and (e):

(a) a magnesium compound represented by formula (I):

$$Mg(OEt)_{2-n}(OMe)_n \quad (I)$$

where Et is an ethyl group, Me is a methyl group and n is a numerical value of from 0.001 to 1

(b) a titanium compound represented by the formula (II)

$$Ti(OR)_qX_{4-q} \quad (II)$$

where X is a halogen atom, R is a hydrocarbon group having from 1 to 10 carbon atoms, q is an integer of from 0 to 4, and a plurality of R's are the same as or different from each other when q is 2 or more, (c) a halogen compound (e) an alcohol, wherein the compound represented by formula (I) is prepared by simultaneously reacting metal magnesium, ethanol, methanol and a halogen and/or a halogen-containing compound comprising at least 0.0001 gram atom of a halogen atom relative to one gram atom of the metal magnesium.

13. The method according to claim 11, wherein the compound represented by formula (I) is prepared by simultaneously reacting metal magnesium, ethanol, methanol and a halogen and/or a halogen-containing compound comprising at least 0.0005 and less than 0.06 gram atom of a halogen atom relative to one gram atom of the metal magnesium.

* * * * *